(12) United States Patent
Ishikawa et al.

(10) Patent No.: US 9,282,923 B2
(45) Date of Patent: Mar. 15, 2016

(54) FLUOROCHROME MATERIAL AND METHOD FOR USING THE SAME

(75) Inventors: Yoshihiro Ishikawa, Tokyo (JP); Haruki Eguchi, Kawasaki (JP)

(73) Assignees: IHI CORPORATION, Tokyo (JP); Yoshihiro Ishikawa, Tokyo (JP)

( * ) Notice: Subject to any disclaimer, the term of this patent is extended or adjusted under 35 U.S.C. 154(b) by 132 days.

(21) Appl. No.: 13/701,157

(22) PCT Filed: May 12, 2011

(86) PCT No.: PCT/JP2011/002651
§ 371 (c)(1),
(2), (4) Date: Nov. 30, 2012

(87) PCT Pub. No.: WO2011/151978
PCT Pub. Date: Dec. 8, 2011

(65) Prior Publication Data
US 2013/0090539 A1    Apr. 11, 2013

(30) Foreign Application Priority Data
Jun. 1, 2010    (JP) ................................ 2010-126021

(51) Int. Cl.

| | |
|---|---|
| A61B 5/00 | (2006.01) |
| A61B 8/00 | (2006.01) |
| A61B 10/00 | (2006.01) |
| A61B 5/1455 | (2006.01) |
| C07C 251/24 | (2006.01) |
| C09B 57/10 | (2006.01) |
| C09K 11/06 | (2006.01) |
| A61K 9/14 | (2006.01) |
| A61K 31/295 | (2006.01) |
| C07F 15/02 | (2006.01) |
| A61K 49/00 | (2006.01) |
| A61K 41/00 | (2006.01) |

(52) U.S. Cl.
CPC .............. *A61B 5/1455* (2013.01); *A61K 9/14* (2013.01); *A61K 31/295* (2013.01); *C07C 251/24* (2013.01); *C07F 15/02* (2013.01); *C09B 57/10* (2013.01); *C09K 11/06* (2013.01); *A61K 41/00* (2013.01); *A61K 49/0017* (2013.01); *C09K 2211/1007* (2013.01); *C09K 2211/187* (2013.01); *Y10T 428/2982* (2015.01)

(58) Field of Classification Search
USPC ........................................................ 424/9.6
See application file for complete search history.

(56) References Cited

U.S. PATENT DOCUMENTS

2003/0108614 A1    6/2003   Volkonsky et al.
2003/0138432 A1*   7/2003   Glazier ...................... 424/178.1
2007/0134338 A1*   6/2007   Subramaniam et al. ...... 424/489
2009/0169484 A1    7/2009   Eguchi et al.
2012/0029167 A1    2/2012   Ishikawa et al.

FOREIGN PATENT DOCUMENTS

| EP | 1114836 A1 | 7/2001 |
|---|---|---|
| JP | 05-009470 A | 1/1993 |
| JP | 2001-010978 A | 1/2001 |
| JP | 2009-173631 A | 8/2009 |
| JP | 2009196914 A | 9/2009 |
| WO | 2008/001851 A1 | 1/2008 |
| WO | 2010058280 A1 | 5/2010 |

OTHER PUBLICATIONS

Johnson et al. (J. Phys. Chem. C 2008, 112, 12272-12281).*
European Saarch Report, European Patent Appln. No. 11789393.3, Jan. 2, 2014, 8 pp.
Appleton, Trevor G., "Oxygen uptake by a cobalt(II) complex—An undergraduate experiment", Journal of Chemical Education, vol. 54, No. 7, Jul. 1, 1997, p. 443-444, XP055093191, ISSN: 0021-9584, DOI: 10.1021/ed054p443.
Woldemariam et al., "Iron(III)-salen damages DNA and induces apoptosis in human cell via mitochondrial pathway", Journal of Inorganic Biochemistry, Elsevier Inc, US, vol. 102, No. 4, Jan. 3, 2008, pp. 740-747, XP022523562, ISSN: 0162-0134, DOI: 10.1016/J.JINORGBIO.2007.11.008.
Qi et al., "anti-Spin-Delocalization Effect in Co-C Bond Dissociation Enthalpies", Organometallics, ACS, Washington, DC, US, vol. 27, No. 12, Jan. 1, 2008, pp. 2688-2698, XP002675419, ISSN: 0276-733, DOI: 10.1021/OM701135C.
Liu et al. "Interaction of Metal Complexes of Bis(salicylidene)-ethylenediamine with DNA", Analytical Sciences, Dec. 2000, vol. 16, pp. 1255-1259.

* cited by examiner

*Primary Examiner* — Michael G Hartley
*Assistant Examiner* — Melissa Perreira
(74) *Attorney, Agent, or Firm* — Volpe and Koenig, P.C.

(57) ABSTRACT

It is an object of the present invention to extend the usefulness of an iron-salen complex. The present invention is a new fluorochrome material containing Chemical Formula (I) below. However, M is Fe, Cr, Mn, Co, Ni, Mo, Ru, Rh, Pd, W, Re, Os, Ir, Pt, Nd, Sm, Eu, or Gd.

Chemical Formula (I)

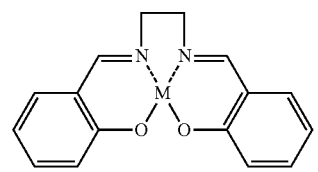

N,N'-Bis(salicylidene)ethylenediamine metal

4 Claims, 2 Drawing Sheets

FLUOROCHROME MATERIAL AND METHOD FOR USING THE SAME

TECHNICAL FIELD

The present invention relates to a fluorochrome material made of a metal-salen complex and a method for using the fluorochrome material.

BACKGROUND ART

Generally, when a drug is administered to a living body, it reaches an affected site and exerts its pharmacological effects at that affected site, thereby exerting its therapeutic effects. On the other hand, even if the drug reaches tissue other than the affected site (that is, normal tissue), it will not be therapeutic.

Therefore, how to guide the drug to the affected site is important. A technique to guide the drug to the affected site is called drug delivery, which has been actively studied and developed recently. This drug delivery has at least two advantages.

One advantage is that a sufficiently high drug concentration can be obtained at the affected site tissue. Pharmacological effects will not be seen unless the drug concentration at the affected site is a constant value or more. The therapeutic effects cannot be expected if the concentration is low.

The second advantage is that the drug is guided to only the affected site tissue and, therefore, adverse reactions to the normal tissue can be inhibited.

Such drug delivery is most effective for a cancer treatment by antitumor agents. Most antitumor agents inhibit the cell growth of cancer cells which divide actively, so that the antitumor agents will also inhibit the cell growth of even the normal tissue in which cells divide actively, such as bone marrow, hair roots, or alimentary canal mucosa.

Therefore, cancer patients to whom the antitumor agents are administered suffer adverse reactions such as anemia, hair loss, and vomiting. Since such adverse reactions impose heavy burdens on the patients, the dosage needs to be limited, thereby causing a problem of incapability to sufficiently obtain the pharmacological effects of the antitumor agents.

Alkylating anti-cancer drugs among such antineoplastic drugs are a generic term for antitumor agents having the ability to combine an alkyl group ($-CH_2-CH_2-$) with, for example, a nucleic acid protein. It alkylates DNA and inhibits DNA replication, causing cell death.

This action works regardless of cell cycles, also works on cells of the $G_0$ period, has a strong effect on cells which grow actively, and tends to damage, for example, bone marrow, alimentary canal mucosa, germ cells, or hair roots.

Moreover, antimetabolite antineoplastic drugs are compounds having structures similar to those of nucleic acids or metabolites in a protein synthesis process, impairs cells by, for example, inhibiting synthesis of the nucleic acids, and specifically acts on cells of a mitotic period.

Furthermore, antitumor antibiotics are chemical substances produced by microorganisms, have actions such as DNA synthesis inhibition and DNA strand breaking, and exhibit antitumor activity.

Also, microtubule inhibitors have antitumor effects by directly acting on microtubules that serve important roles to maintain normal functions of cells, for example, by forming spindles during cell division, locating cell organelles, and transporting substances. The microtubule inhibitors act on cells, which divide actively, and nerve cells.

Moreover, platinum drug inhibit DNA synthesis by forming DNA strands, interchain bonds, or DNA protein bonds. Cisplatin is a representative drug, but it causes severe renal injury and requires a large amount of fluid replacement.

Furthermore, hormone preparation antineoplastic drugs are effective against hormone-dependent tumors. Female hormones or anti-androgen drugs are administered to an androgen-dependent prostatic cancer.

Also, molecular targeted drugs is a treatment targeted at molecules that correspond to molecular biological characters specific to respective malignant tumors.

Moreover, topoisomerase inhibitors are enzymes for temporarily generating breaks in DNA and changing the number of tangles of DNA strands. A topoisomerase inhibitor I is an enzyme that generates breaks in one strand of a circular DNA, lets the other strand pass, and then closes the breaks; and a topoisomerase inhibitor II temporarily breaks both the two strands of the circular DNA, lets other two DNA strands pass between the former two strands, and reconnects the broken strands.

Furthermore, nonspecific immunopotentiators inhibit an increase of cancer cells by activating the immune system.

Most antitumor agents inhibit the cell growth of cancer cells which divide actively, so that the antitumor agents will also inhibit the cell growth of even the normal tissue in which cells divide actively, such as bone marrow, hair roots, or alimentary canal mucosa. Therefore, cancer patients to whom the antitumor agents are administered suffer adverse reactions such as anemia, hair loss, and vomiting.

Since such adverse reactions impose heavy burdens on the patients, the dosage needs to be limited, thereby causing a problem of incapability to sufficiently obtain the pharmacological effects of the antitumor agents. Furthermore, in a worst-case scenario, there is a possibility that the patients might die due to the adverse reactions.

So, it is expected to inhibit the adverse reactions and perform the cancer treatment effectively by guiding the antitumor agents to the cancer cells by means of the drug delivery and allowing the antitumor agents exert the pharmacological effects intensively on the cancer cells. Topical anesthetics have the same type of problem.

Topical anesthetics are used to treat topical itches and pains of, for example, mucosa or skin caused by hemorrhoidal disease, stomatitis, gum disease, cavities, tooth extraction, or operations. Lidocaine (product name: xylocalne) is known as a representative topical anesthetic; however, lidocaine is faster-acting, but has an antiarrhythmic effect.

Furthermore, if lidocaine which is an anesthetic is injected into the spinal fluid when giving spinal anesthesia, lidocaine will spread through the spinal fluid; and in a worst-case scenario, there is fear that lidocaine might reach a cervical part of the spinal cord and thereby cause a respiratory function to stop and bring about critical adverse effects.

So, it is expected to inhibit the adverse reactions and perform the cancer treatment effectively by guiding the antitumor agents to the cancer cells by means of the drug delivery and allowing the antitumor agents exert the pharmacological effects intensively on the cancer cells.

Furthermore, it is also expected to prevent the spread of the topical anesthetic and achieve continued medicinal effects and reduction of the adverse effects by means of the drug delivery.

An example of a specific method for the drug delivery is the use of a carrier. This is to load the carrier, which tends to concentrate on the affected site, with the drug and have the carrier carry the drug to the affected site.

A promising candidate of the carrier is a magnetic substance and there is a suggested method of attaching the carrier, which is the magnetic substance, to the drug and allowing the carrier to be accumulated at the affected site by a magnetic field (see, for example, Patent Literature 1).

However, when using the magnetic substance carrier as the carrier, it has been found that it is difficult to aurally administer the magnetic substance carrier, molecules of the carrier are generally giant, and there are technical problems about binding strength and affinity between the carrier and the drug molecules; and it is originally difficult to achieve the practical use of the magnetic substance carrier.

Therefore, the inventors of the present invention suggested a topical anesthetic in which side chains for giving positive or negative spin charge density are bonded to a basic skeleton of an organic compound, and which has suitability as a whole insofar as the topical anesthetic is guided, by means of magnetic sharing, by an external magnetic field; and if the topical anesthetic is applied to a human body or an animal, it is retained in an area where a magnetic field is applied topically by the magnetic field outside the body and the medicinal effects that the topical anesthetic originally has are exerted on the area. The above-mentioned publication describes the iron-salen complex as an example of such a drug (see Patent Literature 2).

An antitumor drug containing an iron-salen complex is also disclosed (see, for example, Patent Literature 3).

CITATION LIST

Patent Literature

[Patent Literature 1] Japanese Patent Application Laid-Open (Kokai) Publication No. 2001-10978
[Patent Literature 2] WO2008/001851
[Patent Literature 3] Japanese Patent Application Laid-Open (Kokai) Publication No. 2009-173631

SUMMARY OF INVENTION

It is an object of the present invention to extend the usefulness of the iron-salen complex.

In order to achieve the above-described object, the present invention is a new fluorochrome material containing Chemical Formula (I) below.

N,N'-Bis(salicylidene)ethylenediamine Metal

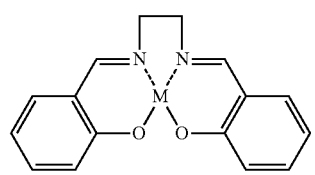

Chemical Formula (I)

However, M represents Fe (iron), Cr (chromium), Mn (manganese), Co (cobalt), Ni (nickel), Mo (molybdenum), Ru (rubidium), Rh (rhodium), Pd (palladium), W (tungsten), Re (rhenium), Os (osmium), Ir (iridium), Pt (platinum), Nd (niobium), Sm (samarium), Eu (europium), or Gd (gadolinium).

Particularly, a compound whose M is iron emits phosphorescence of microwaves ranging from 300 nm to 500 nm. Therefore, as described in Japanese Patent Application Laid-Open (Kokai) Publication No. 2009-173631, the metal-salen complex compound can be made to become fluorescent and affected site tissue may be visually confirmed by administering the metal-salen complex compound represented by Chemical Formula (I) as an antitumor drug to an individual such as a human or an animal, magnetically guiding it to the target cancer tissue, and then irradiating the affected site tissue with laser light or fluorescence when performing surgery to remove the affected site tissue.

Regarding an average particle diameter of the metal-salen complex compound, an excessively large particle diameter might possibly cause the compound to occlude blood vessels. On the other hand, if the particle diameter is small, the compound might possibly lose its magnetic property. Therefore, an appropriate average particle diameter of the compound is 2 to 60 μm, preferably 5 to 20 μm, more preferably 8 to 15 μm, particularly preferably 9 to 12 μm, and optimally 10 μm.

The particle diameter is adjusted within the above-described range during a recrystallization process. For example, in synthesis step 7 described later, it is stated that "[t]he resulting compound was recrystallized in a solution of diethyl ether and paraffin" and the target particle diameter can be obtained by increasing the temperature up to 80 degrees Celsius once before the recrystallization and then spending 12 hours to cool it down to the room temperature.

As the result of examination by the inventor of the present invention, the magnetization property of the metal-salen complex compound changes depending on the particle diameter. If the particle diameter is too small more than necessary, the magnetization property of the metal-salen complex compound is not sufficient; and if such a metal-salen complex compound is administered to the individual such as a human or an animal, there is a possibility that the metal-salen complex compound may not be guided to the target area by the external magnetic field. On the other hand, if the particle diameter is too large more than necessary, there is a possibility that magnetic particles may aggregate in blood vessels.

As described in Japanese Patent Application Laid-Open (Kokai) Publication No. 2009-173631, the iron-salen complex represented by Chemical Formula (I) is useful as an antitumor drug having such a magnetic property that if it is administered to the individual without using a magnetic carrier and an external magnetic field (for example, 0.3 T) is then applied to the individual, the molecules are guided to the area to which the magnetic field is applied.

The new fluorochrome material containing Chemical Formula (I) mentioned above can be obtained according to the present invention as explained above.

DESCRIPTION OF EMBODIMENTS

Production of Metal-Salen Complex (Iron-Salen)

Step 1

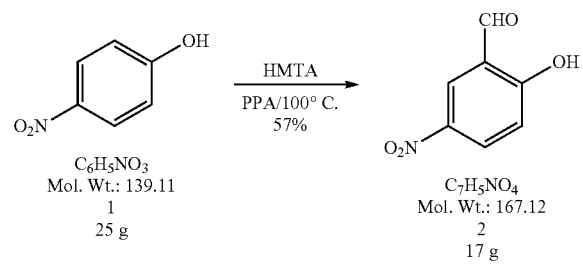

Figure 1:
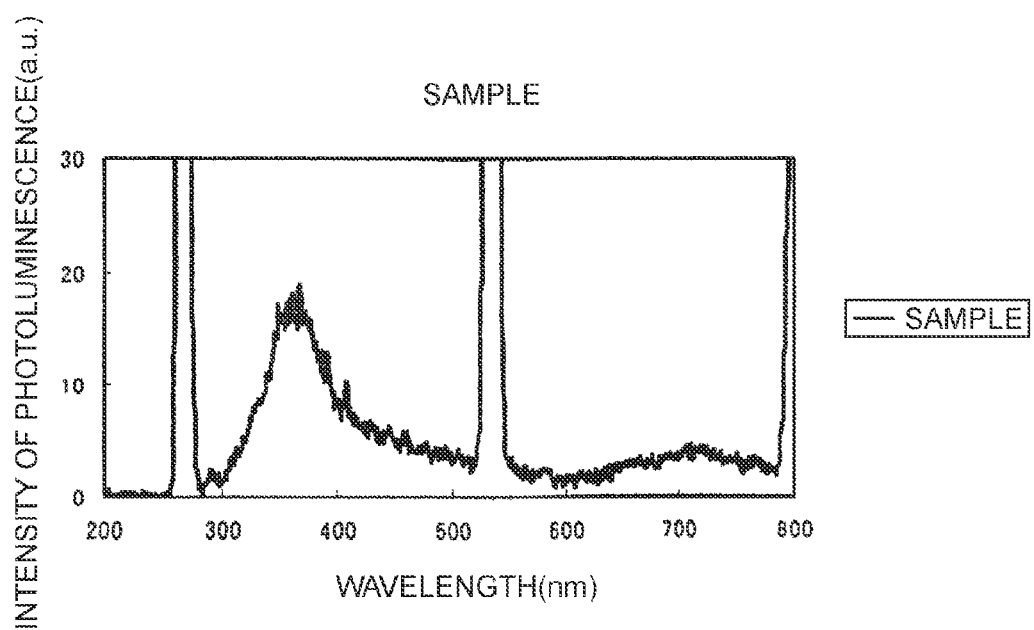
FIG. 1 is a characteristic diagram showing the results of a luminescence test of the metal-salen complex.

A mixture of 4-nitrophenol (Compound 1) (25 g, 0.18 mol), hexamethylene tetramine (25 g, 0.18 mol), and polyphosphoric acid (200 ml) were stirred for one hour at the temperature of 100 degrees Celsius. Then, that mixture was introduced to 500 ml of ethyl acetate and 1 L (liter) of water and stirred until it completely dissolved. Furthermore, when 400 ml of ethyl acetate was added to that solution, the solution separated into two phases. Subsequently, the aqueous phase was removed from the solution which separated into the two phases; and the remaining compound was washed twice with a basic solvent and dried over anhydrous $MgSO_4$. As a result, 17 g of Compound 2 (57% yield) was synthesized.

Step 2

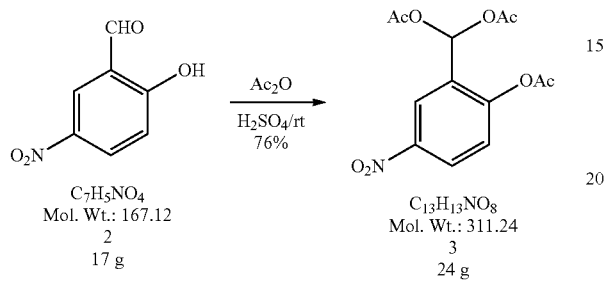

Compound 2 (17 g, 0.10 mol), acetic anhydride (200 ml) and $H_2SO_4$ (minimal) were stirred for one hour at room temperature. The resulting solution was mixed for 0.5 hour in iced water (2 L) to bring about hydrolysis. The resulting solution was filtered and dried in air, thereby obtaining white powder. The powder was recrystallized, using a solvent containing ethyl acetate. As a result, 24 g of Compound 3 (76% yield) was obtained in the form of white crystals.

Step 3

A mixture of carbon (2.4 g) supporting 10% palladium with Compound 3 (24 g, 77 mol) and methanol (500 ml) was reduced over night in a 1.5 atm hydrogen reducing atmosphere. After the reduction was completed, the product was filtered, thereby allowing 21 g of Compound 4 in the form of brown oil to be synthesized.

Step 4, 5

Compound 4 (21 g, 75 mmol) and di(tert-butyl)dicarbonate (18 g, 82 mmol) were stirred over night in anhydrous dichloromethane (DCM) (200 ml) in a nitrogen atmosphere. The resulting solution (Compound 5) was allowed to evaporate in a vacuum and then dissolved in methanol (100 ml). Sodium hydroxide (15 g, 374 mmol) and water (50 ml) were then added and the solution was brought to reflux for 5 hours. The solution was then cooled, filtered, washed with water, and allowed to dry in a vacuum, thereby obtaining a brown compound. The resulting compound was processed twice by flash chromatography using silica gel, thereby obtaining 10 g of Compound 6 (58% yield).

Step 6

Compound 6 (10 g, 42 mmol) was introduced into 400 ml of anhydrous ethanol, the mixture was brought to reflux while heated, and several drops of ethylene diamine (1.3 g, 21 mmol) were added into 20 ml of anhydrous ethanol while stirred for 0.5 hour. The mixture was introduced into a container of ice, where it was cooled and stirred for 15 minutes.

It was then washed with 200 ml of ethanol, filtered, and dried in a vacuum, thereby obtaining 8.5 g (82% yield) of Compound 7.

Step 7

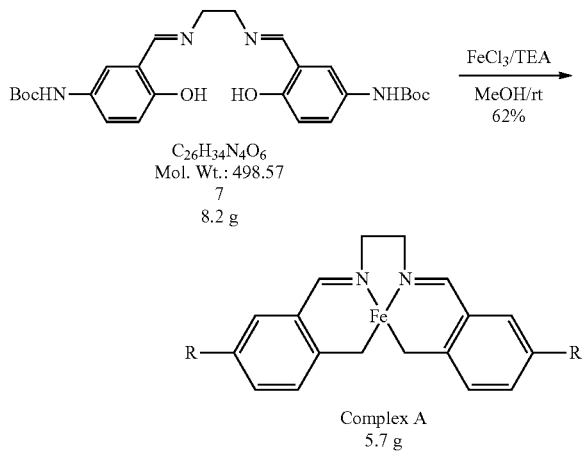

Compound 7 (8.2 g, 16 mmol) and triethylamine (22 ml, 160 mmol) were introduced into dehydrated methanol (50 ml), and a solution of iron (III) chloride ($FeCl_3$) (2.7 g, 16 mmol) added to 10 ml of methanol was mixed for one hour in a nitrogen atmosphere at room temperature, thereby obtaining a brown compound. The brown compound was then dried in a vacuum.

The resulting compound was diluted with 400 ml of dichloromethane, washed twice with a basic solution, dried in sodium sulfate ($Na_2SO_4$), and dried in a vacuum. The resulting compound was recrystallized in a solution of diethyl ether and paraffin, and assay by high performance liquid chromatography revealed 5.7 g (62% yield) of complex A (iron-salen complex) with a purity of 95% or higher.

When a metal complex other than the iron-salen complex is to be used, a chloride of metal other than iron ($MCl_3$: where M is a metal) may be used instead of iron (III) chloride ($FeCl_3$). Incidentally, Japanese Patent Application No. 2009-177112 of the applicant of the present application discloses that a manganese-salen complex, a chromium-salen complex, and a cobalt-salen complex other than the iron-salen complex have such magnetic properties that they can be guided by an external magnetic field. Then, it is also apparent from Japanese Patent Application Laid-Open (Kokai) Publication No. 2009-173631 that the metal iron-salen complex or the like has an antitumor effect.

<Luminescence Test>

A luminescence test by means of photoluminescence measurement was conducted with respect to the iron-salen complex represented by Chemical Formula (I).

The measurement was conducted by using PHOTOLUMINOR-S for high resolution spectral analysis by HORIBA, Ltd. The measurement was performed in a state where the metal-salen was dissolved in chloroform.

The obtained results are shown in FIG. 1. Referring to FIG. 1, it was confirmed that a peak specific to the iron-salen complex represented by Chemical Formula (I) occurred around 380 nm. Incidentally, peaks were confirmed around 270 nm, 530 nm, and 800 nm in FIG. 1, but these are reference peaks for an excitation laser (laser that emits white light by oscillating several wavelengths of RGM at the same time). The peak wavelength varies depending on a crystal shape of the iron-salen complex.

<Particle Diameter Measurement>

The particle diameter of the iron-salen complex of Chemical Formula (I) was measured by using a laser diffraction method. The device used for the measurement was Microtrac particle analysis instruments (MT-3000II by NIKKISO CO., LTD.). A sample was put in a solution of sodium hexametaphosphate; and the resulting solution was dispersed for 10 minutes by using a homogenizer, the sample was then irradiated with laser light, and its diffraction (dispersion) was measured to find the grading. Measurement conditions and measurement results are as follows.

<Measurement Conditions>
Measurement time: 30 seconds
Particle permeability: permeable
Particle shape: nonspherical
Particle refractive index: 1.81
Solvent: water
Solvent refractive index: 1.333

Figure 2:
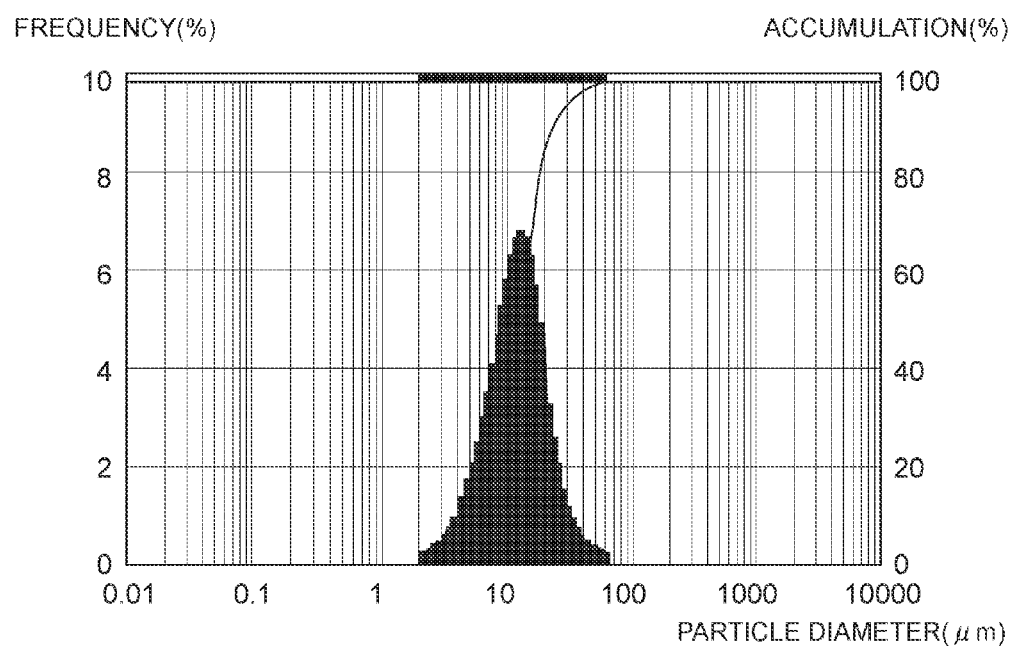
FIG. 2 is a characteristic diagram showing the results of particle diameter measurement of the metal-salen complex.

<Measurement Results>
Measurement results are shown in FIG. 2 and below.
Average particle diameter: 11.79 μm
Standard deviation: 6.289

As a result of the measurement, it was found that the particle diameter of the iron-salen complex was 11.8 μm, which is sufficiently suited for application to individuals.

If a metal-salen complex capable of emitting a fluorescent color such as the aforementioned iron-salen complex is administered to an individual, a magnetic field is applied externally to the individual to guide the metal-salen complex to a target area, and an external light is then applied to the target area as explained above, luminescence of the metal-salen complex can be confirmed.

The invention claimed is:
1. A method comprising:
   administering to an individual a fluorochrome material containing a metal-salen complex represented by Chemical Formula (I);

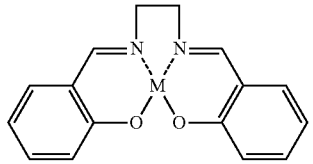

Chemical Formula (I)

N,N'-Bis(salicylidene)ethylenediamine metal,
wherein M is Fe, Cr, Mo, Ru, Rh, Pd, W, Re, Os, Ir, Pt, Nd, Sm, Eu, or Gd, and the metal-salen complex is in the form of a particle having a particle diameter in the range of 2 to 60 μm;
   externally applying a magnetic field to the individual to guide the fluorochrome material to a target area;
   applying external light to the target area, thereby causing the fluorochrome material in the target area to luminesce, with a peak luminous wavelength of the metal-salen complex represented by Chemical Formula (I) around 380 nm;
   confirming luminescence in the target area visually; and
   removing luminescent target area tissue.
2. The method according to claim 1, wherein M in the metal-salen complex represented by Chemical Formula (I) is Fe.

3. The method according to claim 1,
wherein the particle diameter of the metal-salen complex represented by Chemical Formula (I) ranges from 9 to 12 μm.

4. The method according to claim 2,
wherein the particle diameter of the metal-salen complex represented by Chemical Formula (I) ranges from 9 to 12 μm.

* * * * *